United States Patent
Galkin

(10) Patent No.: US 7,251,309 B2
(45) Date of Patent: Jul. 31, 2007

(54) MAMMOGRAPHY CUSHIONING DEVICES AND METHODS

(76) Inventor: Benjamin M. Galkin, 35 Ivy La., Cherry Hill, NJ (US) 08002

( * ) Notice: Subject to any disclaimer, the term of this patent is extended or adjusted under 35 U.S.C. 154(b) by 0 days.

(21) Appl. No.: 11/582,243

(22) Filed: Oct. 17, 2006

(65) Prior Publication Data

US 2007/0019785 A1  Jan. 25, 2007

Related U.S. Application Data

(63) Continuation of application No. 11/246,419, filed on Oct. 7, 2005, now Pat. No. 7,142,631, which is a continuation-in-part of application No. 10/748,891, filed on Dec. 30, 2003, now Pat. No. 6,975,701.

(51) Int. Cl.
*A61B 6/04* (2006.01)

(52) U.S. Cl. ...................................................... 378/37

(58) Field of Classification Search ................. 378/37; 600/427; 128/915, 845

See application file for complete search history.

(56) References Cited

U.S. PATENT DOCUMENTS

| | | | | |
|---|---|---|---|---|
| 4,691,333 A | 9/1987 | Gabriele et al. | ............... | 378/37 |
| 5,063,583 A | 11/1991 | Galkin | ........................ | 378/207 |
| 5,276,726 A | 1/1994 | Galkin | ........................ | 378/207 |
| 5,311,883 A | 5/1994 | Sherman | ...................... | 128/846 |
| 5,377,254 A | 12/1994 | Walling | ........................ | 378/167 |
| 5,394,456 A | 2/1995 | Livingston | ................... | 378/162 |
| 5,406,612 A | 4/1995 | Galkin | ......................... | 378/207 |
| 5,479,927 A | 1/1996 | Shmulewitz | ............ | 128/660.09 |
| 5,541,972 A | 7/1996 | Anthony | ........................ | 378/37 |
| 5,544,238 A | 8/1996 | Galkin | ......................... | 378/207 |
| 5,553,111 A | 9/1996 | Moore et al. | .................. | 378/37 |
| 5,706,327 A | 1/1998 | Adamkowski et al. | ......... | 378/37 |
| 6,049,583 A | 4/2000 | Galkin | .......................... | 378/37 |
| 6,122,542 A | 9/2000 | Lee et al. | ..................... | 600/427 |
| 6,577,702 B1 | 6/2003 | Lebovic et al. | ............... | 378/37 |
| 6,974,255 B1 | 12/2005 | Hixson, Sr. | ................... | 378/208 |
| 6,975,701 B2 | 12/2005 | Galkin | .......................... | 378/37 |
| 2003/0007597 A1 | 1/2003 | Higgins et al. | ............... | 378/37 |
| 2003/0058987 A1 | 3/2003 | Rick et al. | ..................... | 378/37 |
| 2003/0174807 A1 | 9/2003 | Lebovic et al. | ............... | 378/37 |
| 2003/0194052 A1 | 10/2003 | Price et al. | .................... | 378/45 |

(Continued)

FOREIGN PATENT DOCUMENTS

DE 23 35 576 1/1975

(Continued)

OTHER PUBLICATIONS

Galkin, B.M., et al., "The Breast Pillow™: A mammography device for reducing patient discomfort and pain," 2001, 0768BR-e, 1 page.

(Continued)

*Primary Examiner*—Jurie Yun
(74) *Attorney, Agent, or Firm*—Woodcock Washburn LLP

(57) ABSTRACT

Mammography units comprising a compression device, a light transparent panel displaced from a compression surface, and a bolster, as well as compression paddles for use with mammography units are described. Methods for their use in reducing patient discomfort during mammography are also described.

21 Claims, 14 Drawing Sheets

U.S. PATENT DOCUMENTS

| | | | |
|---|---|---|---|
| 2004/0081284 A1 | 4/2004 | Livingston | 378/162 |
| 2005/0113683 A1 | 5/2005 | Lokhandwalla et al. | 600/427 |
| 2006/0050844 A1 | 3/2006 | Galkin | 378/37 |

FOREIGN PATENT DOCUMENTS

| | | |
|---|---|---|
| FR | 2 702 059 | 9/1994 |

OTHER PUBLICATIONS

Galkin, B.M., et al., "The Breast Pillow™: A mammography device for reducing patient discomfort and pain," *Education exhibit presented at the annual meeting of the Radiological Society of North America*, Nov. 25-30, 2001, Abstract 0768BR-e published in Supplement to Radiology, 2001, 221(P), p. 698.

Galkin, B., et al., "The Breast Pillow™: A novel device to reduce patient discomfort and pain during mammography while also measuring compression force(1)," *Med. Physics*, Aug. 2001, 28(8), SU-HH-EXH C-10, 1 page.

Galkin, B.M., et al., "The Breast Pillow™: A novel device to reduce patient discomfort and pain during mammography while also measuring compression force," *Poster exhibit presented at the annual meeting of the American Association of Physicists in Medicine*, Jul. 22-26, 2001, Abstract SU-HH-EXH C-10 published in *Med. Phys.*, 2001, p. 1820.

Berns, E. et al., "Effect of Foam Pads on Mammography Dose Calculation", *Medical Physics, 45th Annual Meeting American Association of Physicists in Medicine*, Aug. 10-14, 2003, 2 pages.

Keshavmurthy, S.P. et al., "Design and Evaluation of an External Filter Technique for Exposure Equalization in Mammography", *Medical Physics*, Aug. 1999, 26(8), 1655-1669.

Kruger, R.A. et al., "Light Equalization Radiography", *Medical Physics*, Jul./Aug. 1990, 17(4), 696-700.

Lam, K.L. et al., "Exposure Equalization Technique in Mammography", *Investigatve Radiology*, 1989, 154-157.

Lam, K.L. et al., "Effects of X-Ray Beam Equalization on Mammographic Imaging", *Medical Physics*, Mar./Apr. 1990, 17(2), 242-249.

Panayiotakis, G. et al., "An Anatomical Filter for Exposure Equalization in Mammography", *European Journal of Radiology*, 1992, 15, 15-17.

Plewes, D.B. et al., "Role of Equalisation Mammography of Dense Breasts", *Medical & Biological Engineering & Computing*, Mar. 1995, 167-173.

Sabol, J.M. et al., "Mammographic Scanning Equalization Radiography", *Medical Physics*, Sep./Oct. 1993, 20(5), 1505-1515.

Sabol, J.M. MSc. et al., "A method for Pratical Equalization Mammography of the Radiographically Dense Breast", *Imaging & Therapeutic Technology*, 1995, 15(5), 1191-1202.

Vyborny, C. M.D., Ph. D. et al., "Foil Filters for Equalized Chest Radiography", *Radiology*, 1984, 524.

S.O.F.T. Paddle® by American Mammographics, http://www.americanmammographics.com/SOFTPaddle.htm, 2 page.

U.S. Appl. No. 60/187,198, filed Mar. 6, 2000, Lebovic et al.

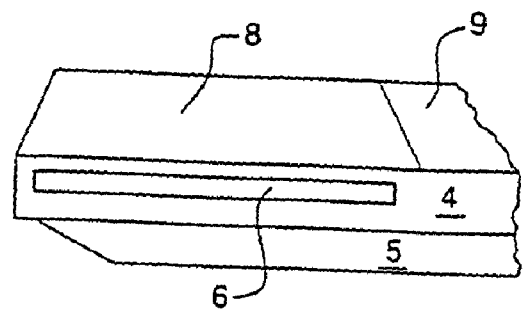
FIG. 3 – PRIOR ART
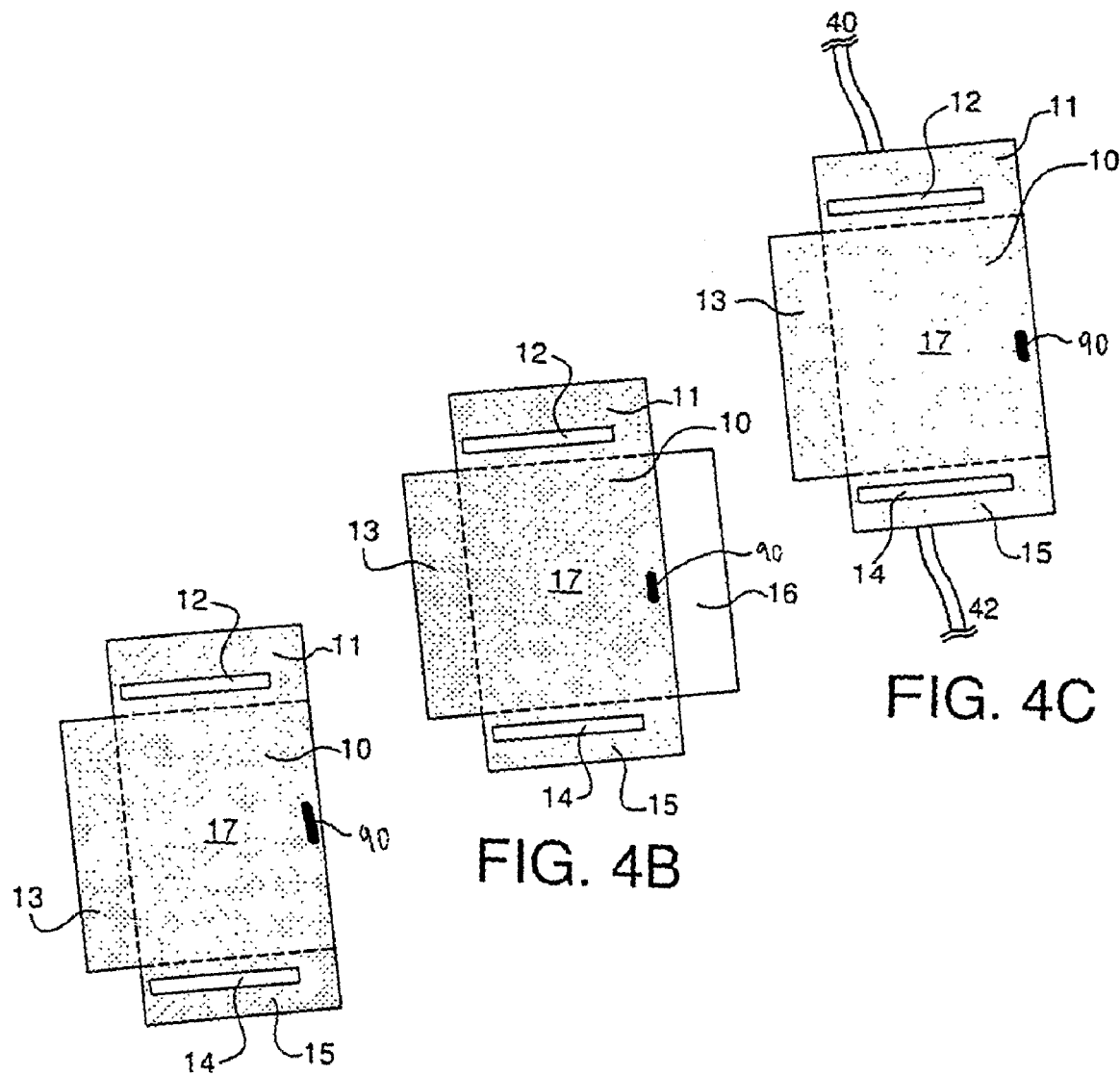
FIG. 4A
FIG. 4B
FIG. 4C

MAMMOGRAPHY CUSHIONING DEVICES AND METHODS

CROSS-REFERENCE TO RELATED APPLICATIONS

This is a continuation of U.S. application Ser. No. 11/246,419, filed Oct. 7, 2005 now U.S. Pat. No. 7,142,631, which is a continuation-in-part of U.S. application Ser. No. 10/748,891, filed Dec. 30, 2003 now U.S. Pat. No. 6,975,701, which is incorporated herein by reference in its entirety and from which priority is claimed.

FIELD OF THE INVENTION

The present invention relates to the field of radiology and particularly to mammography. More specifically, the present invention relates to mammography cushioning devices and methods for use.

BACKGROUND OF THE INVENTION

Mammography is the process of obtaining x-ray images of the human breast for diagnosis or surgery. It involves positioning a patient's breast in a desired orientation against a cassette holder (also known as a "bucky") of a mammography unit, compressing the breast with a compression device (e.g., a compression paddle), and then exposing the breast to x-rays to create a latent image of the breast on an image receptor. After exposure, the compression device is released. The image receptor is usually a film in contact with an intensifying screen contained within a cassette. The cassette is inserted into a cassette holder before every image is taken and removed after every image. The film is removed from the cassette and developed to produce a radiographic image of the breast.

A complete mammographic study usually involves at least two x-ray exposures of each breast. One exposure is a craniocaudal view in which the breast is compressed in a superior-inferior direction, i.e., from the direction of the patient's head downward, against a tube-side surface of the cassette holder. The plane of the tube-side surface of the cassette holder is parallel to the floor and the x-ray beam is directed vertically downward. A second exposure is a lateral or oblique view in which the breast is compressed mediolaterally, i.e., from the direction of the patient's midline sidewise, against the tube-side surface of the cassette holder which is angled, along with the axis of the x-ray beam, relative to the floor.

The compression device includes a rectangular flat plate, called a compression paddle or a compression plate, which is attached to the mammography unit between an x-ray tube assembly and the cassette holder (also known as a "bucky"). The edges of the paddle or plate are turned upward away from the cassette holder to provide a smooth curved surface for patient comfort. The compression paddle is usually made of thin, light-transparent, plastic that absorbs only a small fraction of the incident x-ray beam. The compression paddle is moved either manually or by power drive to apply a compression force to the breast, thereby flattening the breast against the cassette holder to a near uniform thickness. U.S. Pat. No. 6,049,583 issued to the present inventor discusses methods and apparatus for measuring compression force in mammography. During compressing and imaging, parts of the patient's body come into contact with the compression paddle. After x-ray exposure, the compression force is released for patient comfort. Sometimes, pads that are not light transparent are used in conjunction with compression paddles, but by doing so, the visible light that reaches the tube-side surface is blocked which hinders proper placement of the breast.

To properly position the patient's breast in a desired orientation, a technologist is guided by a light beam originating from the x-ray tube assembly that passes through a collimator and the compression paddle and illuminates the area of the cassette holder that will be exposed to x-rays, i.e., the imaging area. As is well known in the field, to properly position the breast, the patient's chest wall or other regions of the body, depending on the desired view, are brought into tight contact with the rigid surfaces of the cassette holder, its edges, and corners. This procedure has the effect of forcing the patent's anatomy to contour to the shape of the cassette holder, which often causes patient discomfort and pain.

Oftentimes, overlapping internal structures are present within the breast tissue that can obscure their delineation in a radiographic image. As a result, it is often necessary to reposition the breast slightly in order to arrive at a diagnosis. This requires repositioning the patient for each view with the attendant discomfort.

During positioning, compressing, and imaging, parts of the patient's body come into contact with the cassette holder. The cassette holder is a rectangular, box-like device that has a flat tube-side surface against which the breast is compressed, a flat outer surface along one edge of the tube-side surface which contacts the patient's chest wall or torso, and two flat side surfaces opposite each other along the other edges that can come into contact with other parts of the patient's anatomy such as the underarm and axilla. Each of the side surfaces has an opening, typically rectangular, to a cassette tunnel. The openings are used for insertion and removal of the cassette. The tube-side surface includes an imaging area, which is transparent to x-rays, located directly above the cassette as it resides in the cassette holder, and where the breast is positioned during imaging, and a solid section which is not transparent to x-rays. Within the cassette holder is an antiscatter grid assembly. The cassette holder is held in position on the x-ray unit by slidably engaging to a support member. Because the surfaces of the cassette holder may come into contact with blood or other infectious material, they must be able to withstand contact with the chemical agents usually used for disinfecting purposes. Cassette holders come in different sizes depending on the size film to be used.

It is well known that many women find the procedure for obtaining a mammogram to be uncomfortable and for some, even painful. Methods to provide patient comfort during the examination involve adding cushioning material to the surfaces of the cassette holder and/or the compression paddle.

It is well known to those in the art that image quality of a mammogram is highly dependent on beam quality, which is a function of several factors including the kilovoltage (kVp) impressed across the anode and cathode of the x-ray tube, the material of the x-ray target (e.g., molybdenum), the inherent filtration of the tube (e.g., beryllium), and the material and thickness of added filtration (e.g., molybdenum). Beam quality is measured in terms of half value layer in aluminum (HVL). Adding material in the path of the x-ray beam has a similar effect to adding filtration, for example, HVL increases. Most modern mammography units automatically adjust x-ray exposure factors, including kVp, according to HVL. Increasing kVp decreases image contrast, and thus reduces image quality.

The degree to which HVL is increased by the addition of a material in the path of the x-ray beam depends on its linear attenuation coefficient, "μ," and thickness, "t,". Linear attenuation coefficient is related to physical density. For example, material described as being made of foam can have a density that varies over a wide range. For example, polyurethane foam can have densities of between about 1.8 and about 2.6 pounds per cubic foot.

Moreover, foam cushioning comes in various thicknesses. The firmness of foam is measured in units of Indentation Force Deflection (IFD). which is determined by indenting (compressing) a foam product 25% of its original height. The amount of force, measured in pounds, required to compress the foam is its 25% measurement. The IFD of cushioning foam can range from between about 21 and about 45 pounds.

With respect to the thickness of the foam, it is known in the art that the sharpness of a radiographic image depends on the object to film distance. The shorter the distance the sharper the image. This is an important consideration when attempting to identify images of breast calcifications which are probably the most important diagnostic indicator of early breast cancer. Interposing cushioning material between the breast and the surface of the cassette holder increases the distance between the calcifications and the film and decreases the sharpness of their images.

Since different kinds of foam can be supplied with varying thicknesses and firmnesses, the application of equal compression force to different cushioning materials can drastically impact arriving at a proper diagnosis. Without intending to be bound by theory, this is likely caused by different distances between the calcifications and the film depending on the cushioning material used which result in different degrees of image sharpness. Knowing exactly what outside factors have impacted a mammogram can be an important consideration in arriving at a correct diagnosis.

Subject to a woman's family health history, women are encouraged to obtain their first mammogram at around age 40 and annually thereafter. In reading and analyzing mammograms, images of a current examination are compared with previous examinations. A radiologist or other medical professional looks for the appearance of and/or changes in diagnostic markers such as micro-calcifications and other internal structures. The difficulty in reading mammograms is that changes in these images can be very subtle and depend in large measure on image quality. Other factors that affect image quality are motion of the breast during x-ray transmission and the range of optical contrast in the image. Motion of the breast is inversely affected by the magnitude of compression force applied by the compression paddle, a larger force reduces movement of the breast. If less compression force could be used, however, then the examination would be less uncomfortable for the patient.

The range of optical contrast in the image depends on several factors including the level of x-ray exposure. For patients with dense breasts, the peripheral region of the breast is often too dark, making it difficult to identify diagnostic features in this area. The usual method to improve visibility in this region is to bright light the film, i.e. increase the light intensity behind the film, but this can reduce contrast perception. Other methods to overcome this problem have been suggested including the use of different kinds of x-ray attenuators positioned between the compression paddle and the breast or under the breast, e.g. a water bag or a solid, elastic, unit density plastic, but these devices are sometimes difficult to implement. Other methods have been described including, for example, the use of different kinds and shapes of x-ray filters positioned between the x-ray tube and image receptor and adjusting the quality and/or the intensity of the x-ray beam using sensors and computers to determine the attenuation and shape of the breast. For a variety of reasons none of these other methods are in general use.

Since a wide variety of cushioning materials may be used in mammography, including some that can have a negative effect on image quality, there is a need for a viewer, e.g., a technologist or a radiologist or other medical professional, be able to determine from the mammogram, for example, that cushioning material was used and the type of cushioning. There is also a need that the mammogram contain a permanent record regarding the nature of the cushion material used.

Further, there remains a great need for comfort devices for use during mammography which can minimize or eliminate the pain and discomfort experienced by the patient. To be useful in clinical practice such devices must also not add significantly to the cost of the examination. There remains a great need to provide an indication on a mammogram to alert the viewer that the quality of the breast image may have been compromised by the use of a comfort device. There also exists a need to provides information to a medical professional, e.g. a technologist or radiologist, regarding the use of comfort devices without compromising the cushioning effect of the materials. In addition, there is a need for comfort materials for compression devices that still allow visible light to be transmitted to allow for proper positioning of a breast. There is a need for a device and method to limit motion of the breast without excessive compression force. And there remains a need for a quick, simple, inexpensive way to improve the visibility of the peripheral region of the breast on mammograms.

SUMMARY OF THE INVENTION

Mammography comfort devices and methods for reducing patient discomfort and pain during mammography are provided by the present invention. Such devices cushion the patient against contact with surfaces of a cassette holder (bucky) and/or a compression paddle that cause patient discomfort and pain.

Comfort devices for use with a mammography unit bucky each comprise an x-ray transparent compressible pad and a bolster comprising compressible material; wherein the bolster is separate from the compressible x-ray transparent pad; and wherein the bolster retains the compressible x-ray transparent pad on the bucky when the bolster and the compressible x-ray material are assembled on the bucky. The x-ray transparent compressible pad comprises a partially radiopaque identifier that is permanently affixed to the x-ray transparent compressible pad, and the first partially radiopaque identifier comprises indicia which impart information about the x-ray transparent compressible pad onto a mammogram. The bolster can further comprise a vent to permit passage of air upon, for example, assembly or contact with a patient. The bolster can also further comprise an opening that permits a mammography unit cassette to pass therethrough. A disposable x-ray transparent cover can be used in conjunction with the comfort devices, where the cover is sized to substantially fits over the pad itself, the bolster itself, or both. The cover can further comprise radiopaque identifier. It may also be useful to have an x-ray transparent position marker on the pad.

A bolster for use with a mammography unit bucky comprises a compressible material; wherein the bucky comprises a tube-side surface; a first side surface substantially perpendicular to the tube-side surface; a second side surface opposite the first side surface; and an outer surface substantially perpendicular to the tube-side surface, the first side surface, and the second side surface; wherein the bolster substantially covers the first side surface, the second side surface; and the outer surface. In some instances, it is desirable that the height of the bolster exceeds the height of the bucky when the bolster is assembled on the bucky. The bolster may further comprise a vent to permit passage of air upon, for example, assembly or contact with a patient. Also, it may be desirable that the bolster comprises a non-porous surface and/or a layer of adhesive. Additionally, the bolster can comprise an opening that permits a mammography unit cassette to pass therethrough. The bolster can be used in combination with an x-ray transparent compressible pad that substantially covers the tube-side surface. Moreover, the pad may comprise a partially radiopaque identifier that is permanently affixed to the x-ray transparent compressible pad and the first partially radiopaque identifier comprises indicia which impart information about the x-ray transparent compressible pad onto a mammogram.

In a detailed embodiment, mammography units comprise a bucky; a comfort device comprising an x-ray transparent compressible pad and a bolster; wherein the bolster is separate from and in contact with the pad, and when assembled together, the bolster substantially retains the pad on the tube-side surface of the bucky; and an x-ray source, a compression device, and a support column to which the bucky is secured.

Methods for reducing patient discomfort during a mammography are provided, comprising securing a bucky to a mammography unit; securing a comfort device comprising an x-ray transparent compressible pad and a bolster that comprises a compressible material over the bucky; and positioning a patient such that the comfort device is disposed between the patient and patient contact surfaces of the bucky; and administering a mammography comprising compressing a breast of the patient.

Kits are provided that comprise at least two disposable x-ray transparent covers and a comfort device, wherein the comfort device comprises an x-ray transparent compressible pad and a bolster that comprises a compressible material; wherein the bolster is separate from the x-ray transparent pad and comprises a first bolster surface, a second bolster surface, and a third bolster surface, wherein the first, second, and third bolster surfaces partially surround the perimeter of the x-ray transparent pad; and wherein each of the covers substantially fits over the pad, the bolster, or both. Either the pads or the covers or both can comprise a partially radiopaque identifier.

In another detailed embodiment, a mammography unit comprises a mammography unit compression device comprising a paddle, a light transparent panel that is displaced from a compression surface of the paddle by a gap of gas, and a bolster that comprises a compressible material and substantially surrounds the perimeter of the light transparent panel; an x-ray source, a bucky, a support column to which the bucky is secured and to which the compression device is adjustably attached; wherein the compression device is located between the x-ray source and the bucky. The light transparent panel can further comprise a vent, a partially radiopaque identifier, and/or non-radiopaque position markings. The bolster can further comprise a vent. In addition, it may be useful to construct the bolster of more than one type of compressible material. For example, the bolster can comprises a first compressible material having a first indentation force deflection value and a second compressible material having a second indentation force deflection value that is different from the first indentation force defection value.

Other examples include mammography unit compression devices comprising a paddle and an x-ray transparent compressible pad comprising an opening that is light transparent. The pad can comprise a partially radiopaque identifier that is permanently affixed to the x-ray transparent compressible pad and comprises indicia, the indicia comprising information about the x-ray transparent compressible pad.

Other methods for reducing patient discomfort during a mammography comprise: securing a light transparent panel over a mammography unit compression paddle with a bolster that comprises a compressible material and substantially surrounds the perimeter of the light transparent panel; positioning a patient's breast on a bucky; and administering a mammogram comprising compressing the breast between the compression paddle and the bucky and transmitting x-rays through the breast. The light transparent panel can comprise a vent that would permit the flow of a gas through the vent and onto the patient's skin. It is preferable that the gas, for example air, is warmer than room temperature to provide additional comfort to the patient.

Another embodiment of a comfort device for use with a mammography unit bucky is a retainer comprising a stretchable strip of x-ray transparent compressible material that fits over the peripheral edge of a breast on the bucky to hold the breast in place during exposure. Less compression force is required when such a retainer is used, thereby reducing patient discomfort. A further embodiment of a comfort device used with a mammography unit bucky is a retainer comprising a stretchable strip of x-ray attenuating compressible material that comprises x-ray attenuation properties similar to that of soft tissue. This retainer serves a dual purpose. When stretched over the peripheral edge of a breast on the bucky, it holds the breast in place during exposure, while the x-ray attenuating properties serve as an exposure equalizer to reduce the optical density of the peripheral region of the breast on a mammogram. Anchors can be provided to removably affix the retainers of the present invention to the bucky. The retainers can be located on the bucky in a location outside of an imaging area, and then be moved into place around the periphery of the breast as needed. The retainers can further comprise identifying, radiopaque indicia.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which:

FIG. 3 is an enlarged schematic view of a typical cassette holder.

FIG. 4A is a top view of a comfort device in accordance with an embodiment of the invention with optional openings for a cassette holder to pass through, flattened to show sections for covering patient-contact surfaces of a cassette holder; FIG. 4B depicts the comfort device of FIG. 4A comprising an optional section for holding the comfort device in place on the cassette holder in accordance with an embodiment of the present invention; FIG. 4C depicts the comfort device of FIG. 4A comprising optional fasteners for holding the comfort device in place on the cassette holder in accordance with an embodiment of the present invention; FIGS. 4A, B, and C also show a radiopaque identifier.

DETAILED DESCRIPTION OF ILLUSTRATIVE EMBODIMENTS

Figure 1:
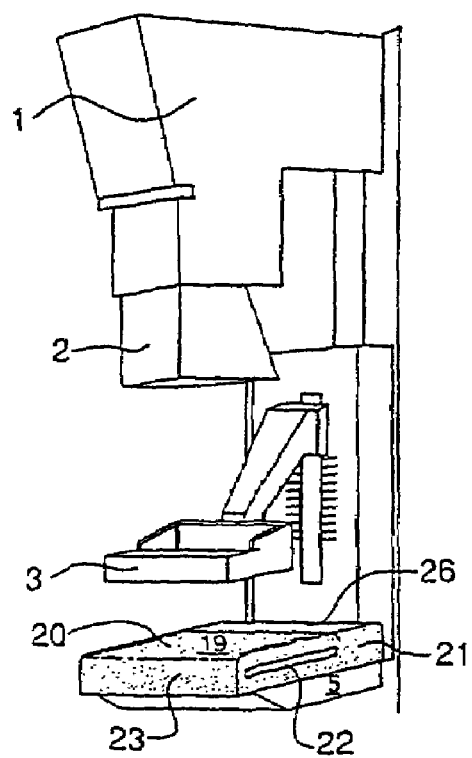
FIG. 1 is a schematic oblique view of a section of a mammography unit illustrating the position of a cassette holder relative to a compression paddle in accordance with an embodiment of the present invention.

This invention describes devices and methods used to minimize and/or eliminate patient discomfort and pain during mammography. For example, comfort devices that comprise a pad separate from a bolster piece that is used to retain the pad in position are provided. Having the pad separate from the bolster provides flexibility in their manufacture. Also, different parts of the devices can be fabricated of different materials to control the magnitude of compression force exerted on the breast. The separate format provides for flexibility in configuring comfort devices for various sizes and shapes of compression devices found on different mammography units.

In accordance with the present invention, comfort devices are provided comprising a bolster and a pad. The bolster comprises a strip of compressible material for cushioning the front and two side surfaces of the cassette holder (bucky). The pad, formed as a separate piece from the bolster, comprises an x-ray transparent compressible material. When assembled together, the bolster is in contact with the pad to substantially fix the location of the pad in place on the imaging surface of the bucky. The bolster can contain openings to facilitate passage of a cassette therethrough when the bolster is assembled with a bucky that is film-based, that is the bucky receives a mammography cassettes holding x-ray film. In one embodiment, the height of the bolster is greater than the height of the side surfaces of the bucky so that when attached to the side surfaces, for example, the top of the bolster projects above the plane of the imaging surface and serves to retain the pad in position. In other examples, a disposable x-ray transparent cover is used in conjunction with the comfort device.

In some instances it may be desirable to fabricate the pad and the bolster with the same material. Because the bolster is not in the path of the diagnostic x-ray, however, it may be desirable or economical to fabricate the strip out of a material that is different from the pad material. For example, the bolster may be made of a less expensive material than that of the pad, where the material of the bolster need not be x-ray transparent since the bolster is not intended to be in the imaging area. Moreover, in some instances the compressible pad may have non-porous surfaces that can be disinfected and reused, while the bolster, made of a less expensive material, may have porous surfaces which requires the use of a new bolster for each patient. In other embodiments, use of a disposable cover along with the comfort devices, which could have porous surfaces, also permit re-use of the pads, panels, and bolsters to reduce per patient costs accrued with use of the devices.

Exemplary embodiments include pads that comprise a partially radiopaque identifier. In preferred embodiments, the identifier is internal to the pad. It may be also be desirable to have an external marker positioned on the pad to correctly orient the pad on the cassette holder so that the indicia appears in the correct location on the mammogram. This external marker can be, for example, a visible, x-ray transparent mark on the surface of the pad, a cutout along any surface or edge of the pad, or an indentation along any surface or edge of the pad. Disposable covers may also comprise radiopaque identifiers.

In yet another embodiment the bolster can contain one or more air vents to allow air to escape, for example, as the pad is affixed to the surface of the cassette holder, or, for example, when a patient presses against the bolster. In another embodiment, a surface of the bolster can have an adhesive layer for attachment to the front and side surfaces of the cassette holder and for attachment to the edges of the pad.

Kits are provided that comprise at least two disposable x-ray transparent covers and a comfort device, wherein the comfort device comprises an x-ray transparent compressible pad and a bolster that comprises a compressible material; wherein the bolster is separate from the x-ray transparent pad and comprises a first bolster surface, a second bolster surface, and a third bolster surface, wherein the first, second, and third bolster surfaces partially surround the perimeter of the x-ray transparent pad; and wherein each of the covers substantially fits over the comfort device as a whole, or the pad or the bolster individually as desired. The pads can comprise a partially radiopaque identifier. The covers can also comprise a partially radiopaque identifier.

Comfort devices for mammography unit compression devices are also provided, comprising a light transparent panel that is displaced from a compression surface of a compression paddle by a gap of gas, and a bolster that comprises a compressible material and substantially surrounds the perimeter of the light transparent panel. The light transparent panel can comprise a vent to permit the flow of air or other gas to the patient's skin. It may be desirable to provide a source of warm air for soothing purposes. The light transparent panel can comprise a partially radiopaque identifier for imparting information about the panel onto a mammogram. In addition, it may be desirable to have non-radiopaque position markings on the panel to facilitate placement of a breast on the imaging surface, or on a pad located on the imaging surface.

A bolster used in conjunction with the light transparent panel can be made of one type of material or, in some instances, more than one compressible material. When more than one type of material is used, it is preferable that each material have a different indentation force deflection (IFD) value to permit the panel to retract at an angle upon compression against a breast.

Other comfort devices for use on a mammography unit compression device can comprise x-ray transparent compressible material and a light transparent opening to permit light to transmit through onto the imaging surface of a bucky, or onto a pad located on the imaging surface of the bucky. This compressible material having an opening can also be used in conjunction with a bolster to keep the material in place on a compression paddle.

Methods for reducing patient discomfort include assembling a comfort device with a bucky or a compression paddle, or both; positioning a patient such that the comfort device is disposed between the patient and patient-contact surfaces, and administering a mammogram. When a component of the comfort device comprises a partially radiopaque identifier comprising indicia, methods also include recording the indicia onto the mammogram. Recording the indicia onto the mammogram can be done, for example, radiographically or electronically or manually.

Methods may further include placing a disposable cover over the comfort device. When the disposable cover comprises a partially radiopaque identifier comprising indicia, methods further include recording the indicia of the disposable cover, which can impart any type of information, onto a mammogram. Although it is preferable to place the disposable cover over the comfort device, it may be desirable in certain instances to place a cover comprising indicia underneath x-ray transparent pads or light transparent panels. Recording the indicia onto the mammogram can be done, for example, radiographically or electronically or manually.

Regarding indicia, it may be desirable to provide information including, but not limited to, the physical properties of a comfort device, such as density or thickness, the location of the device, the manufacturer of the device, and/or the date of manufacture. In addition, it may be useful for pads to have unique serial numbers, that may, for example, aid in tracking re-use of the pads. In accordance with the present invention, information can be provided on the mammogram in an area away from an image of the breast. For example, information about a comfort device that is located on a cassette holder (a bucky) can be positioned in one area of the mammogram and information about a comfort device that is located on a compression paddle can be positioned in another area of the mammogram. Comfort devices containing identifiers used for cassette holders may further comprise cassette holder openings to permit unimpeded placement of a film cassette within the cassette holder. Reference to "cassette holder" and "bucky" means the device that holds an image receptor for the creation of a mammogram, regardless of whether the image receptor is film-based or digital.

An identifier as used by the present invention is partially radiopaque such that identifying indicia can be either x-ray transparent or radiopaque, and the remaining portion of the identifier would be radiopaque or x-ray transparent, respectively. By reference to the radiopaque nature of an identifier, it is understood that the identifier may not be completely radiopaque, but its radiopacity would be sufficiently different from the radiopacity of the surrounding materials, e.g., x-ray transparent compressible materials or x-ray transparent covers, so as to be recordable, e.g. radiographically, on a mammogram. The identifier can comprise a variety of radiopaque materials, e.g., paper, plastic, or metal. In such an embodiment identifying indicia would be x-ray transparent. If desired, in another embodiment, identifying indicia can be imprinted with radiopaque ink onto x-ray transparent compressible material or x-ray transparent covers.

In another example, by reference to an existing bucky, a comfort device comprising compressible material which is transparent to x-ray is placed over the tube-side surface of a bucky, and a bolster is secured to its side surfaces and outer surface. In this way, the patient-contact surfaces are cushioned. The patient-contact surfaces include, but are not limited to a tube-side surface, an outer surface, a first side surface, and a second side surface. In some embodiments, the bolsters are provided with openings for unimpeded placement of cassettes within the cassette holder of a film-based bucky. In addition, the openings are positioned so that insertion and removal of cassettes does not interfere with the functioning of an antiscatter grid. Upon positioning of the patient's breast on an imaging area of the tube-side surface and subsequent compression, the patient's body is then protected from the rigid surfaces and sharp edges of the bare cassette holder by the presence of the comfort device.

Compressible material used in accordance with the present invention may be constructed of varying materials that overlay the tube-side surface of the cassette holder (or bucky) and/or the compression paddle. For example, it may be desirable to use materials of differing total linear attenuation values to obtain different optical densities on a mammogram. It also may be desirable to use multiple layers of compressible material.

Compressible material may include, but is not limited to, polyurethane, polyolefin materials, polyethylene materials, polypropylene materials, and rubber foam. Forms of compressible material include, but are not limited to foam, bubble wrap, anti-static, air core, nylon barrier core, tubing, and matrix. For example, low density polyurethane foams provide resiliency and cushioning characteristics suitable to reduce patient discomfort. Bubble wrap, is a further example of material that is compressible and provides cushioning. Furthermore, various forms of high and low density polyurethane foams could comprise at least one chamber suitable for inflation. Although rubber foam is compressible, it is preferably suitable for surfaces other than the tube-side due to its potential to interfere with the transmission of x-rays.

Comfort devices in accordance with the present invention are amenable to a wide variety of cassette holder shapes and sizes. Given the adaptability of various compressible materials, comfort devices are constructed to fit around various-sized cassette holders and contain openings to permit insertion and removal of various-sized cassettes. Although allowance is made for the use of conventional x-ray films, it is understood that solid state imaging x-ray systems, which do not comprise cassette tunnels, comprising rigid surfaces and sharp edges and corners that contact the patient would also be amenable to embodiments of the present invention.

Figure 2:
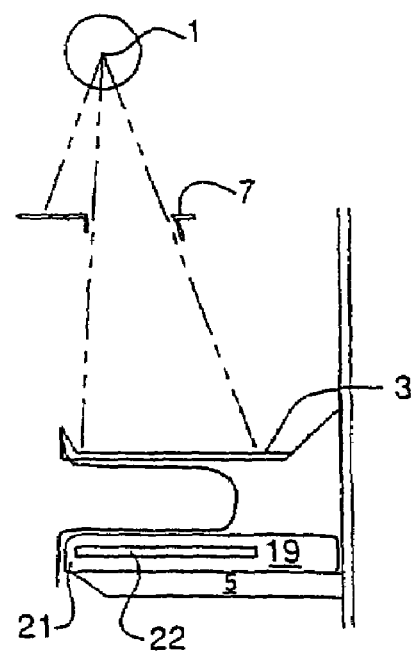
FIG. 2 is a schematic lateral view of FIG. 1 depicting a compressed breast positioned on a cassette holder showing the edge of the cassette holder in contact with the patient's torso.

Referring now to the drawings wherein reference numerals refer to like elements, FIGS. 1 and 2 depict two views of a mammography unit in accordance with an embodiment of the present invention having an x-ray tube 1 that produces x-ray beams (not numbered) connected to a cone 2 that houses a collimator 7. The collimator 7 restricts the size and shape of the x-ray beams in any plane perpendicular to the axis of the x-ray beam. The x-ray beam also passes through a compression paddle 3. Below the compression paddle 3 is a cassette holder 19, which comprises a tube-side surface containing an imaging area 20 and a solid area 26, and a cassette tunnel opening 22. Generally, a cassette tunnel located below the imaging area houses an antiscatter grid and a cassette. The cassette holder 19 is held in place by a support member 5 and slidably engages with a support column (not numbered). X-ray beams pass through imaging area 20 to expose a film in the cassette. The solid area 26 is typically not transparent to x-ray beams and secures the cassette holder to the support column. A patient's breast (not numbered) is positioned on the imaging area 20 of the tube-side surface of the cassette holder 19 and is compressed by the compression paddle 3.

FIG. 3 in an enlarged schematic view of a typical cassette holder 4 positioned on a support member 5, comprising a cassette tunnel 6, an imaging area 8, and a solid area 9.

FIG. 4A is a top view of a comfort device 17 in accordance with the invention with optional openings, flattened, to show sections 10, 11, 13, and 15 for covering patient-contact surfaces of a cassette holder, depicted, for example, in FIG. 3. In one example, a comfort device 17 is fabricated with a compressible material. Compressible material is preferably low Z elastic matrix material. An identifier 90 is partially radiopaque such that information about the compressible material can be imparted onto a mammogram.

In another example, as shown in FIG. 4B, the comfort device of FIG. 4A is depicted with optional section 16 which is an extension of the compressible material that can be adapted with methods for retaining the compressible material in place on the cassette holder. Furthermore, there is no limitation on the material used to fabricate section 16. Although compressible material may be used to facilitate ease of manufacture of the comfort device, it is understood that oftentimes section 16 need not be x-ray transparent, because x-ray beams do not need to penetrate that area, nor compressible, because a patient typically does not contact that area. Section 16 can be integral with the comfort device or attached separately.

In yet a further example, as shown in FIG. 4C, the comfort device of FIG. 4A is depicted with optional fasteners 40 and 42 which secure the device by wrapping around the underside of the support member 5. One fastener is shown on each opposite side of the comfort device, however, it is contemplated that multiple fasteners are suitable for attaching along either side. Furthermore, one fastener can be used which secures to an opposite side of the comfort device.

In one example, fasteners can be straps that meet underneath the support member and tie together. In another example, fasteners can engage with each other using hook and loop fasteners. Yet another embodiment includes fasteners that can be one-piece elastic bands which are fixed to opposite sides of the comfort device. The fasteners can be fabricated of any material suitable for fastening and unfastening. For ease of manufacture, however, it may be desirable to fabricate the fasteners out of the compressible material of the comfort device. Fasteners can be integral with the comfort device or attached separately.

Figure 5:
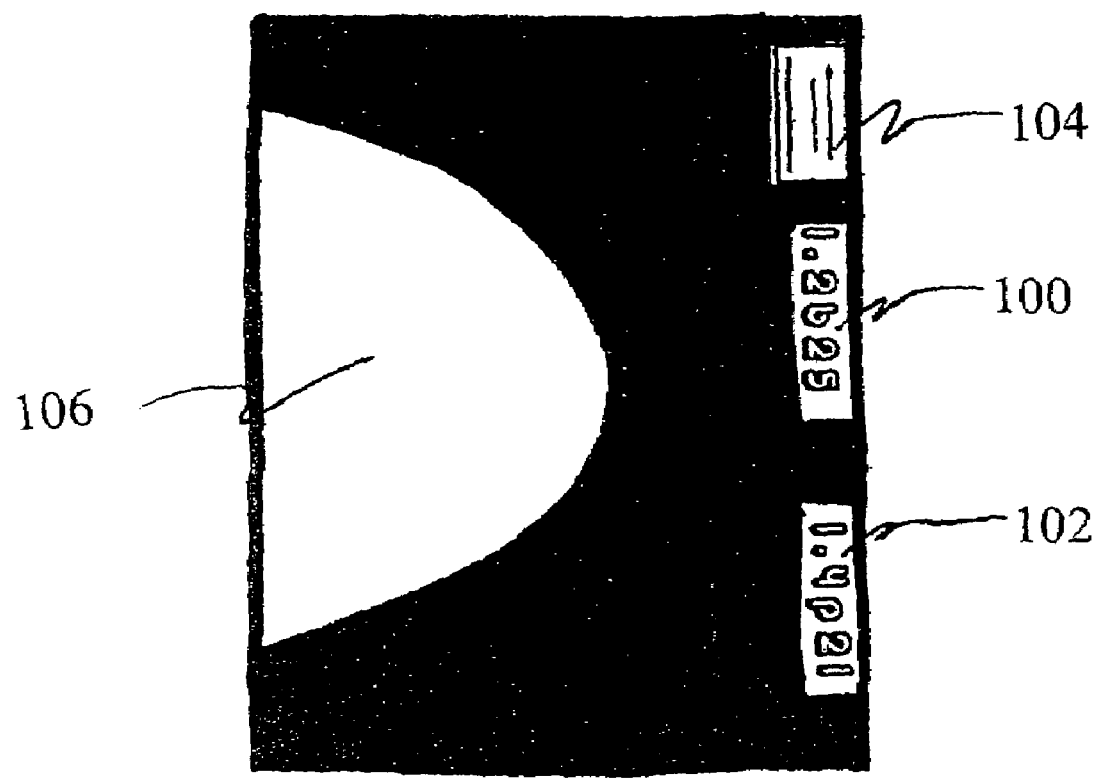
FIG. 5 is a schematic mammogram obtained using the comfort devices comprising partially radiopaque identifiers.

FIG. 5 is a schematic mammogram obtained using comfort devices comprising partially radiopaque identifiers according to the present invention. An image of a breast 106 is shown on the mammogram. Quality control information and patient identifying information 104 can be transferred onto the mammogram electronically by a technologist. In accordance with the present invention, identifying information 100 pertaining to a comfort device used on a tube-side surface and/or patient-contact surfaces of a cassette holder is imparted onto the mammogram by the use of a partially radiopaque identifier. Identifying information pertaining to a comfort device used on patient-contact surfaces of a compression paddle holder 102 is imparted onto the mammogram by the use of a partially radiopaque identifier. Information imparted by indicia is practically unlimited, as it may be desirable to provide information about the device's manufacturer, date of manufacture, physical properties, and/or location. Physical properties may include, but are not limited to, physical density and/or compressibility.

Figure 6:
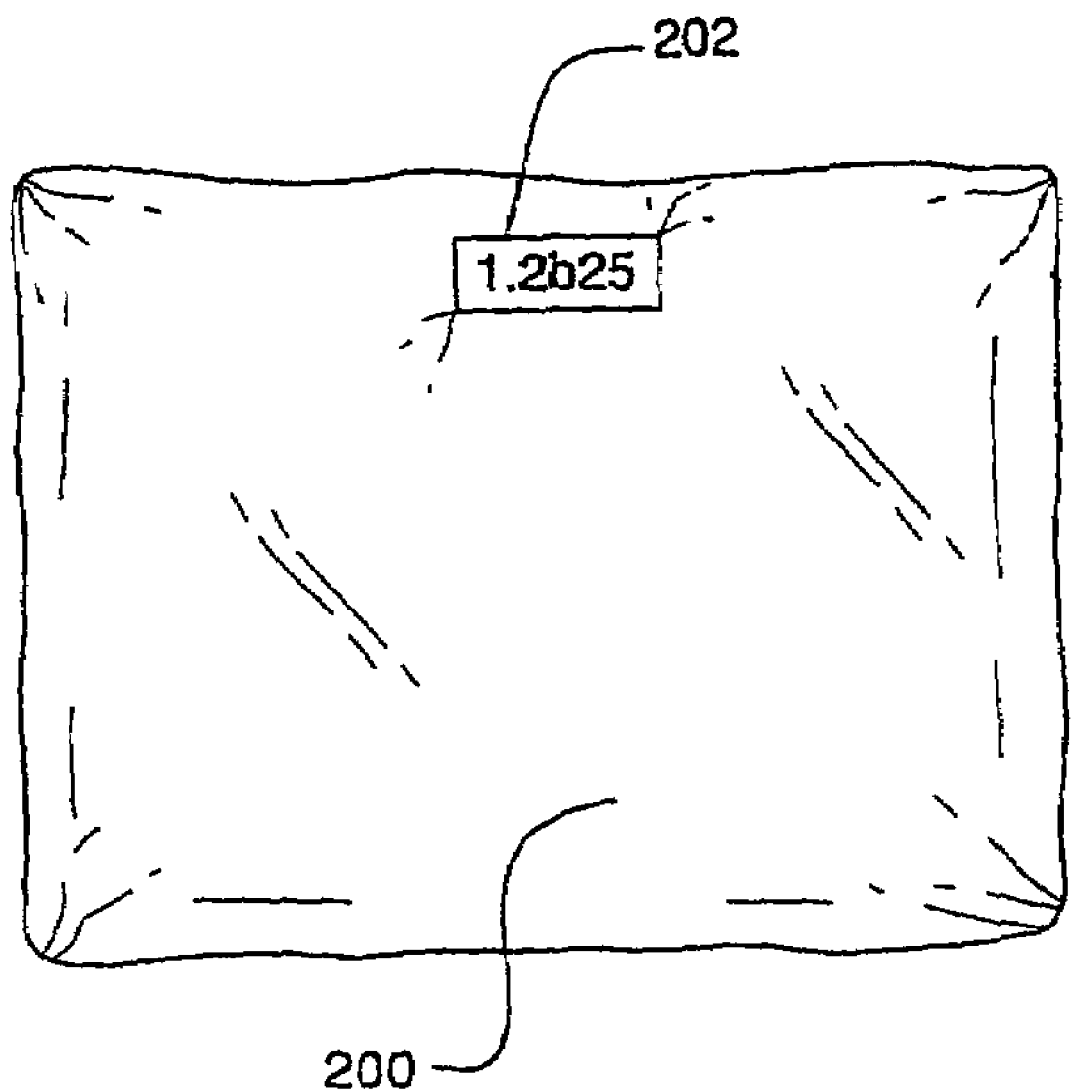
FIG. 6 is an x-ray transparent cover comprising indicia.
Figure 7A:
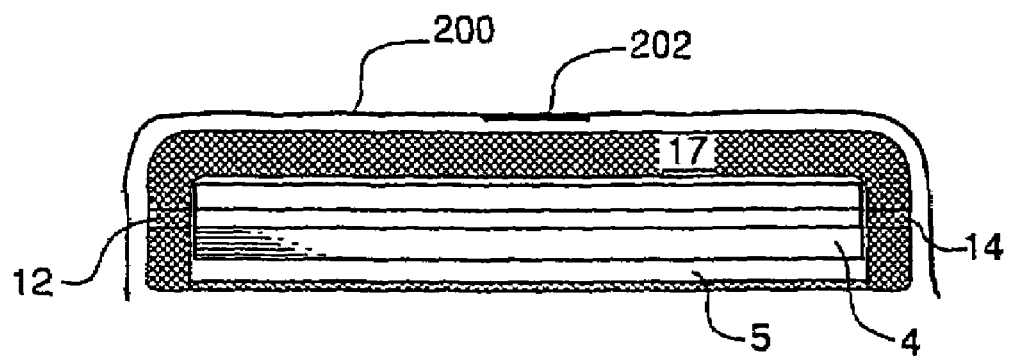
FIG. 7A is an example of an x-ray transparent cover comprising indicia that can be draped over a cushioned cassette holder.
Figure 7B:
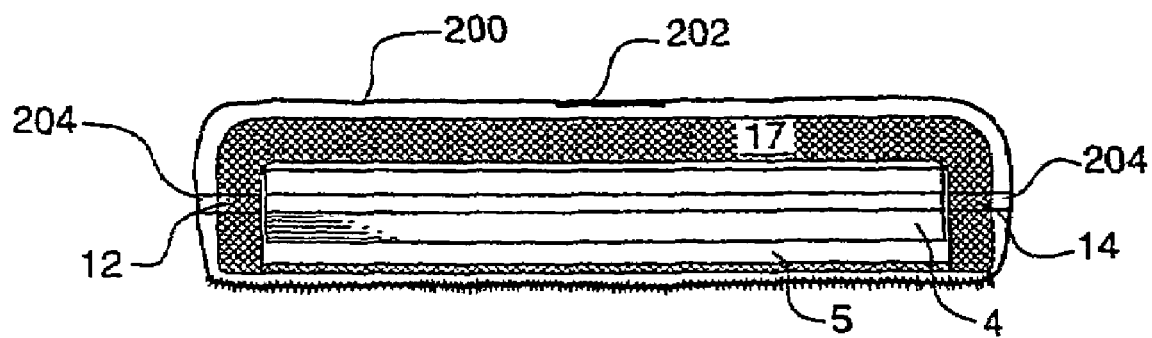
FIG. 7B is an example of an x-ray transparent cover comprising indicia that can be fitted over a cushioned cassette holder and support arm, where the cover has optional side openings.
Figure 8:
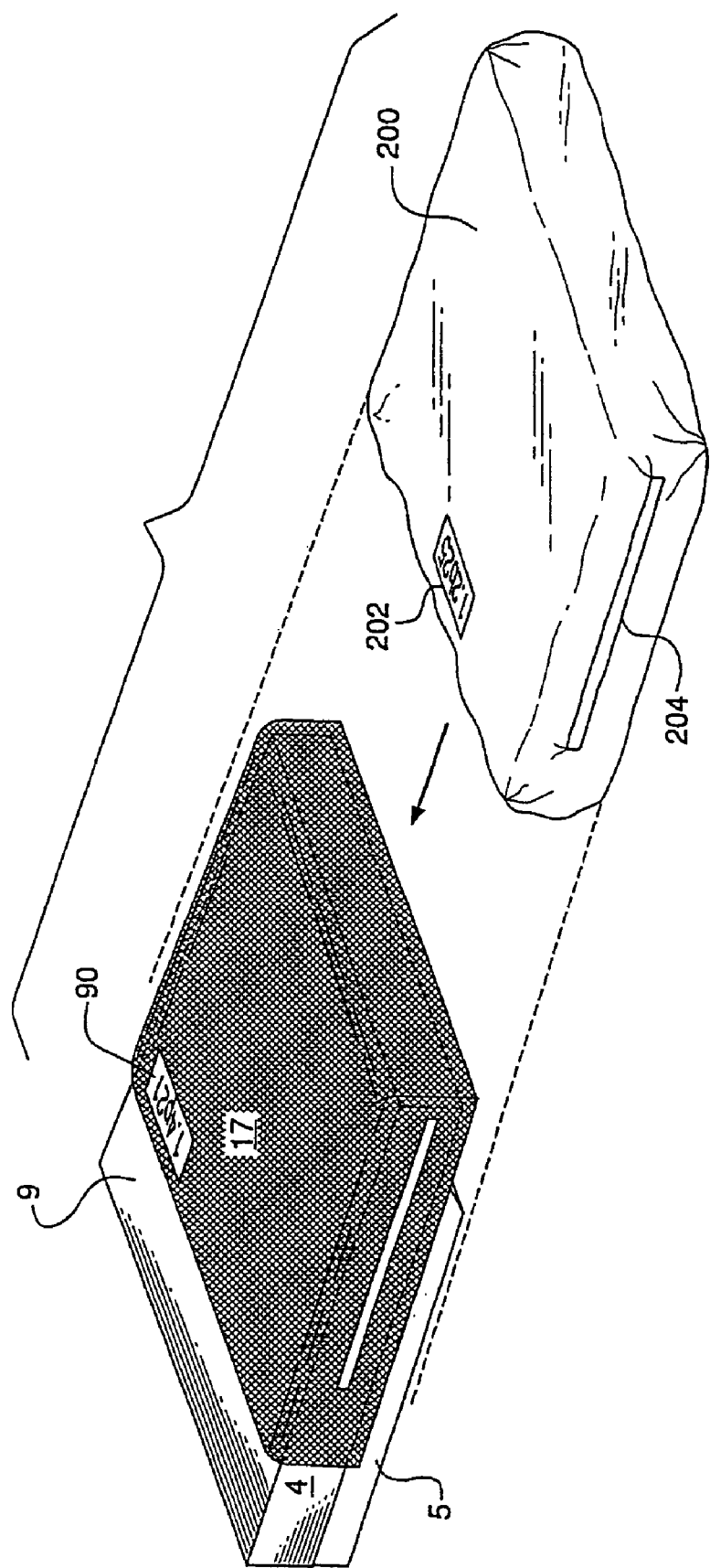
FIG. 8 is an x-ray transparent cover comprising indicia which is offset from a cassette holder which has a compressible x-ray transparent material.

Location of an identifier on a mammogram is preferably outside the area of where the breast is imaged. The partially radiopaque identifier can be located, either permanently or temporarily, for example, on a top surface of an x-ray transparent compressible material, or on a bottom surface, or even within the body of the material. Should more than one layer of compressible material be used, an identifier can be located between the layers. The identifier can also be removably attached to the compressible material, using a radiotranslucent fastener, for example tape. In some instances, it may be desirable to locate the identifier on a surface of the compression paddle or cassette holder or both. As shown in FIG. 6, one or more identifiers 202 can also be located on or within an x-ray transparent cover 200 which in turn can be positioned below or above the compressible material as desired. FIG. 7A depicts one embodiment exemplifying a combination of an x-ray transparent cover 200 comprising indicia 202 which is draped over the compressible material 17 of a cassette holder 4 which is positioned on a support arm 5. Openings 12 and 14 are provided in the compressible material, but due to the draped-nature of the transparent cover 200, corresponding openings in the cover are optional. FIG. 7B shows another embodiment of an x-ray transparent cover 200 comprising indicia 202 which fits around a cassette holder 4 having compressible material 17 wherein the cassette holder 4 is positioned on a support arm 5. The transparent cover 200 optionally comprises at least one opening 204 which is adapted to permit a mammography unit cassette to pass therethrough and can conform to surround the compressible material 17 and support arm 5. FIG. 8 shows an x-ray transparent cover 200 comprising indicia 202 and an optional opening 204, the cover being offset from a cassette holder 4 having compressible material 17, which optionally also has indicia 90. An identifier can simply be a radiopaque material, for example metal (or plastic or paper) which is placed on a comfort device before a mammogram is taken. Indicia which impart information about the comfort device can be x-ray transparent when the rest of the identifier is radiopaque. On the other hand, should the indicia be radiopaque, then the remaining material of the identifier would be radiotranslucent.

Figure 9A:
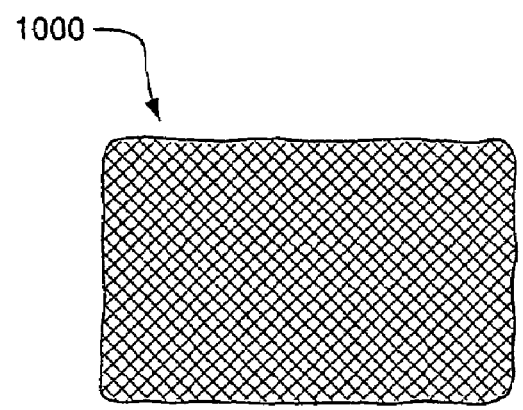
FIGS. 9A, 9B, and 9C, in accordance with the present invention, depict components of a comfort device, with FIG. 9A showing a top view of a compressible pad, and FIGS. 9B and 9C showing side views of exemplary bolsters.
Figure 9B:
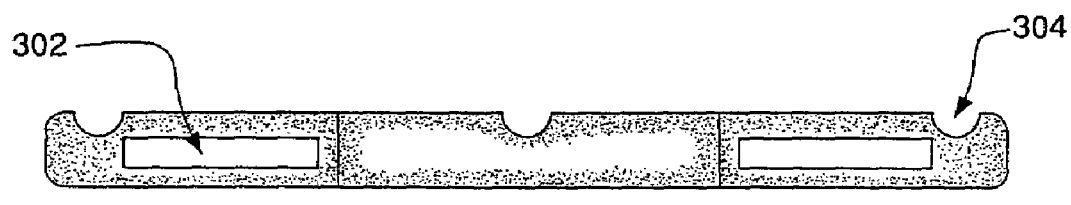
Figure 9C:
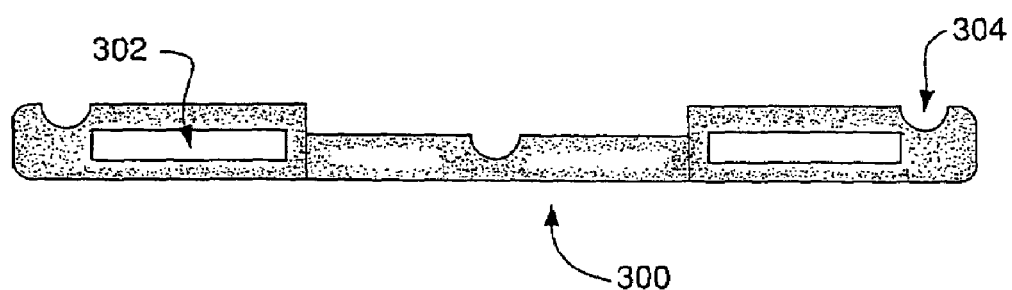

FIGS. 9A, 9B, and 9C, in accordance with the present invention, depict components of a comfort device. A top view of a compressible pad 1000 is provided in FIG. 9A. Side views of bolsters 300 are provided in FIGS. 9B and 9C. An opening 302 for a mammography unit cassette is optionally provided in the bolsters. A vent 304, for the release of air or any gas, in the bolster is optional. In some embodiments, it may be desirable to have an adhesive or other suitable fastener for attaching the bolster to the sides of the cassette holder and/or the compressible pad. In FIG. 9B, the height of the bolster is substantially uniform and is generally formed to surround three sides of a compressible pad. In FIG. 9C, the height of the bolster is non-uniform to allow for a pad that drapes over the outer surface of the bucky. In this example, the bolster frames two sides of the compressible pad, thereby allowing the compressible pad to drape over one portion of the bolster.

Figure 10A:
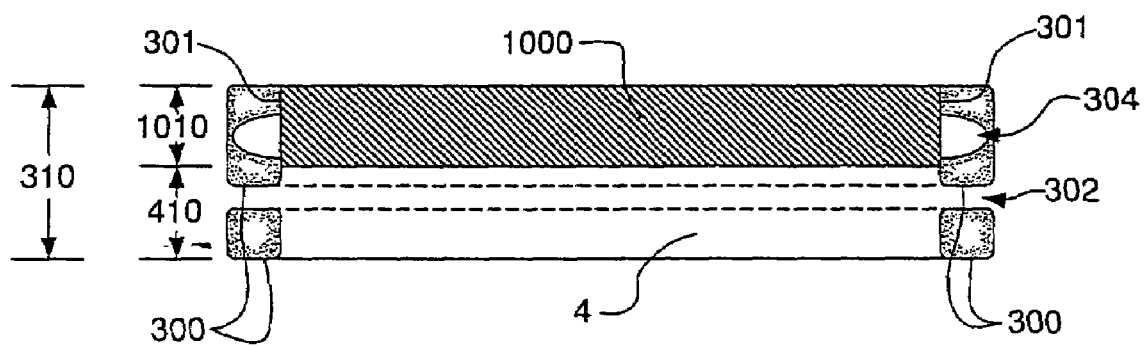
FIG. 10A is a side view of a comfort device assembled with a cassette holder wherein the bolster's height exceeds the height of the cassette holder.

FIG. 10A is a side view of a comfort device assembled with a cassette holder, the bolster 300 is attached to side surfaces of the cassette holder, for example via a strip of adhesive 301 and the compressible pad 1000 is in place on the tube-side surface of the cassette holder. The height of the bolster 310 exceeds the height of the cassette holder 410 by an amount 1010. The amount 1010 need not be exactly the height of the compressible pad 1000. In this embodiment, when the bolster is assembled with the cassette holder, the bolster projects above the top plane of the cassette holder and substantially holds the cushioning pad 1000 in place on the cassette holder 4. The bolster optionally incorporates a vent 304 to facilitate, for example, the escape of, for example, air from between the compressible pad 1000 and the bolster 300 during assembly and/or use. There is an optional opening 302 for a mammography cassette to pass through.

Figure 10B:
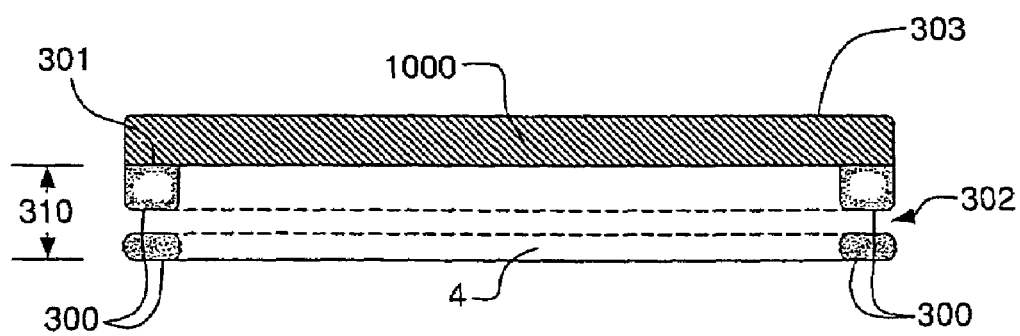
FIG. 10B is a side view of a comfort device assembled with a cassette holder wherein the bolster is substantially the same height as the cassette holder.

FIG. 10B depicts another embodiment of the comfort device comprising a compressible pad 1000 and a bolster 300 in place on a cassette holder 4. The bolster has a height 310 that is essentially the same as the height of the cassette holder 4. There is an optional opening 302 for a mammography cassette to pass through. At least one top surface of the bolster optionally comprises a strip of adhesive 301 to substantially hold the compressible pad 1000 in position. There is also an optional strip of adhesive 303 between the compressible pad 1000 and the bucky 4.

Figure 11:
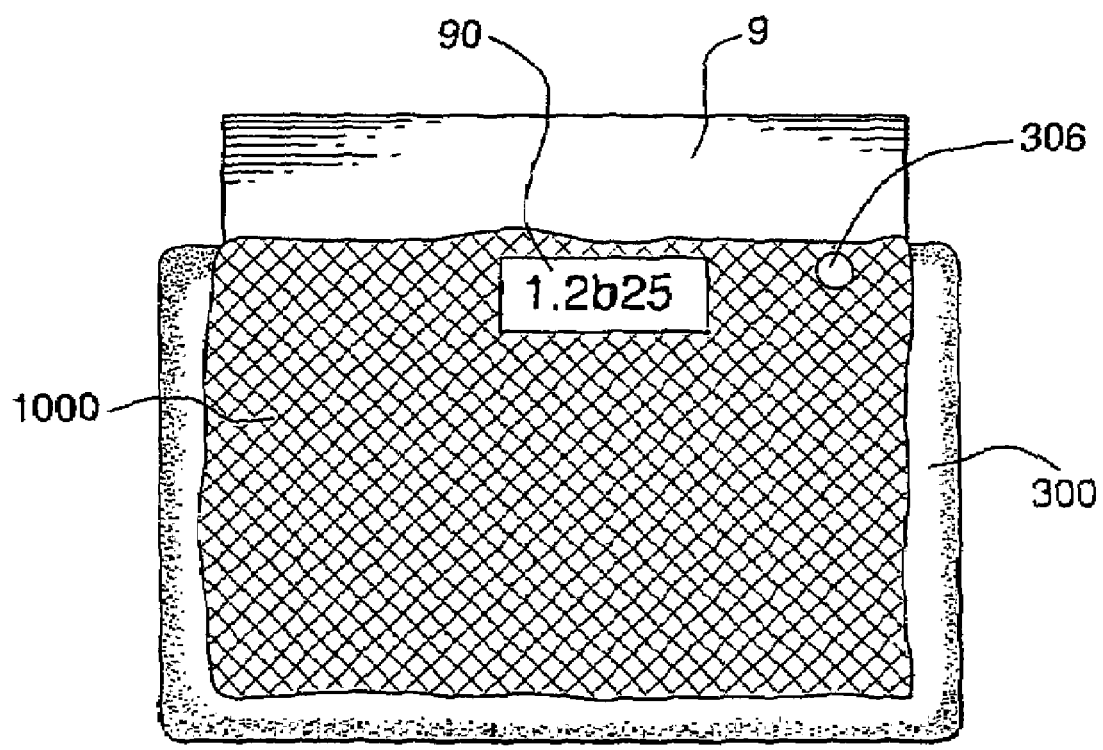
FIG. 11 depicts a top view of a comfort device assembled with a cassette holder.

FIG. 11 depicts a top view of a comfort device assembled with a cassette holder having a solid area 9. In this embodiment, the compressible pad 1000 comprises a permanently attached identifier 90 and a position (orientation) marker 306. The compressible pad 1000 is substantially held in position on the cassette holder by the bolster 300. The position marker 306 facilitates proper positioning of the indicia provided by the identifier 90 onto a mammogram.

Figure 12A:
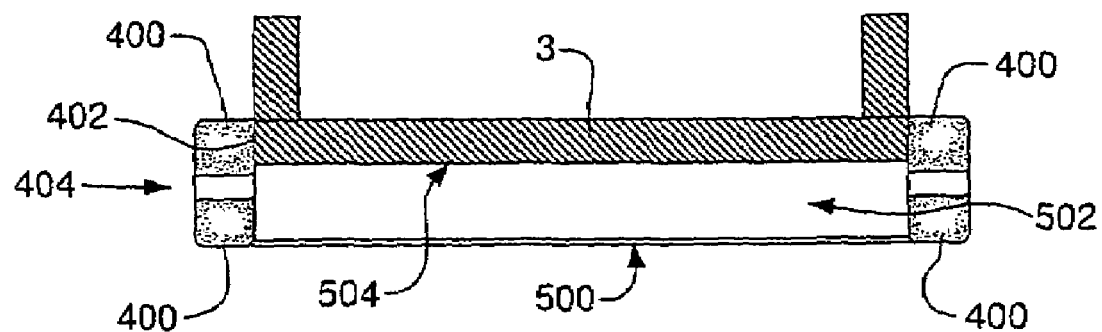
FIGS. 12A and 12B depict schematic views of a comfort device assembled with a compression paddle, before and after compression, respectively.

FIG. 12A shows a schematic view of a comfort device comprising a light transparent panel 500 and a bolster 400, the comfort device being assembled with a compression paddle 3 of a mammography unit. The light transparent panel 500 is displaced from a compression surface 504 the compression paddle 3 by a gap 502 of any gas, for example air. FIG. 12A depicts a schematic of the relative positions of the light transparent panel 500 and bolster 400 to the paddle 3 before compression. An optional fastener 402, for example a strip of adhesive or complementary strips of hook and loop fasteners, is located between the bolster 400 and the compression paddle 3. An optional fastener (not shown), for example a strip of adhesive or complementary strips of hook and loop fasteners, is located between the bolster 400 and the light transparent panel 500. The panel can turn upward at the edges for patient comfort.

Figure 12B:
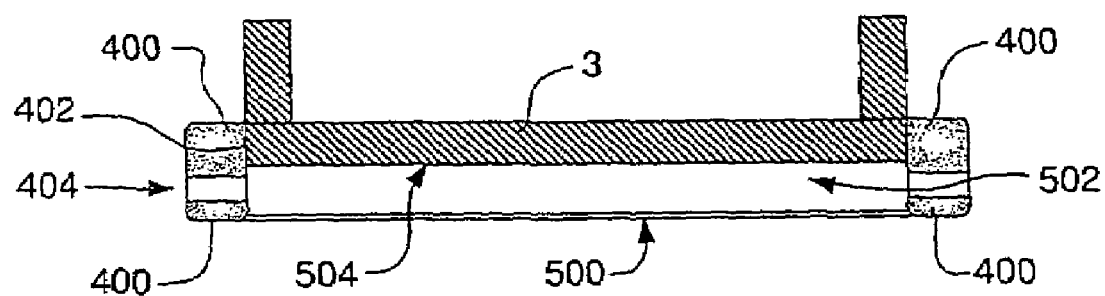
Figure 13:
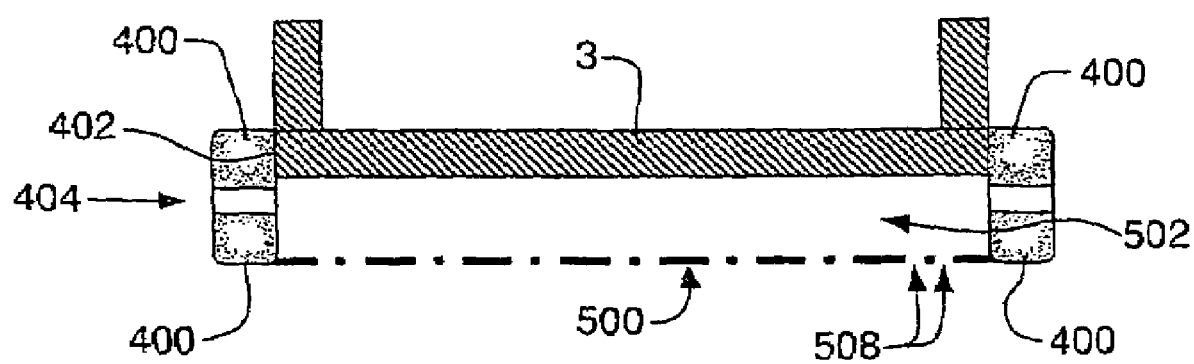
FIG. 13 depicts a schematic view of an exemplary comfort device assembled with a compression device.

FIG. 12B depicts a schematic of the relative positions of the light transparent panel 500 and bolster 400 to the compression surface 504 and paddle 3 after compression. In FIG. 12B, the gap 502 is smaller than the gap 502 shown in FIG. 12A. The light transparent panel is preferably a semi-rigid plastic material. In FIG. 13, the semi-rigid light transparent panel optionally comprises vents 508 to permit air or other suitable gas to pass from the gap 502 through the vents 504 and, for example, to contact a patient's skin. The panel can turn upward at the edges for patient comfort. In FIGS. 12A, 12B, and 13, the bolster 400 wraps around the paddle 3, and the bolster can extend up the sides of the paddle as practical to permit the bolster to be securely attached to the paddle.

Figure 14A:
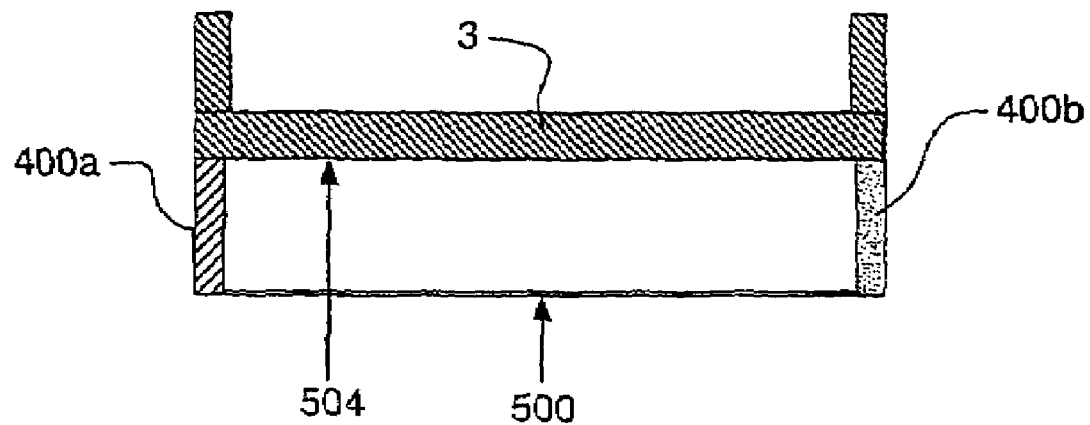
FIGS. 14A and 14B show a schematic view of an exemplary comfort device assembled with a compression device, before and after compression, respectively.
Figure 14B:
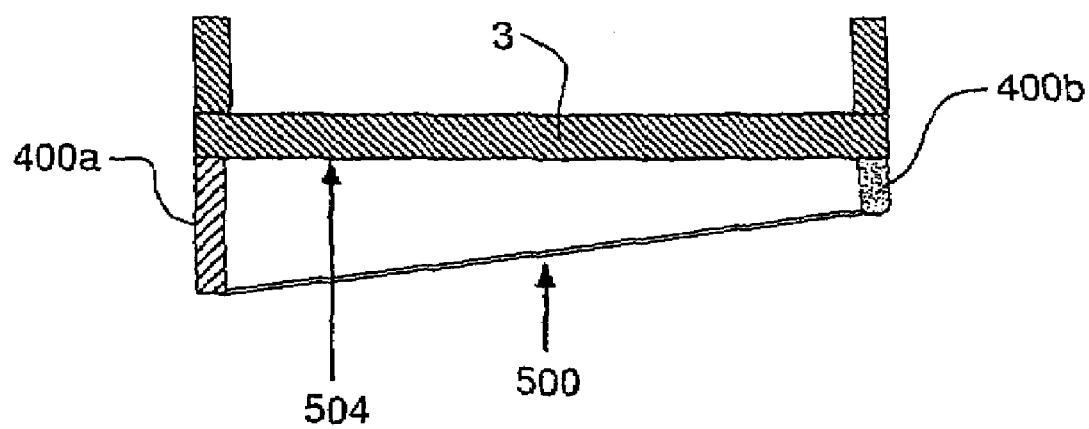

FIGS. 14A and 14B show a schematic view of an exemplary comfort device assembled with a compression device 3, before and after compression, respectively. In FIGS. 14A and 14B, a panel bolster comprising two compressible materials (400a and 400b) having two different indentation force deflection (IFD) values is shown. The light transparent panel 500 is substantially held in place by the bolster, comprising compressible materials 400a and 400b. Prior to compression, as shown in FIG. 14A, the light transparent panel 500 is separated from a compression surface of the compression paddle 3 by a substantially uniform distance. Upon compression, as shown in FIG. 14B, due to the differing IFD values, the light transparent panel 500 is separated from the compression paddle 3 by an uneven distance. The compressible material having a smaller IFD value 400b will compress more readily than a material having a larger IFD value 400a.

Figure 15A:
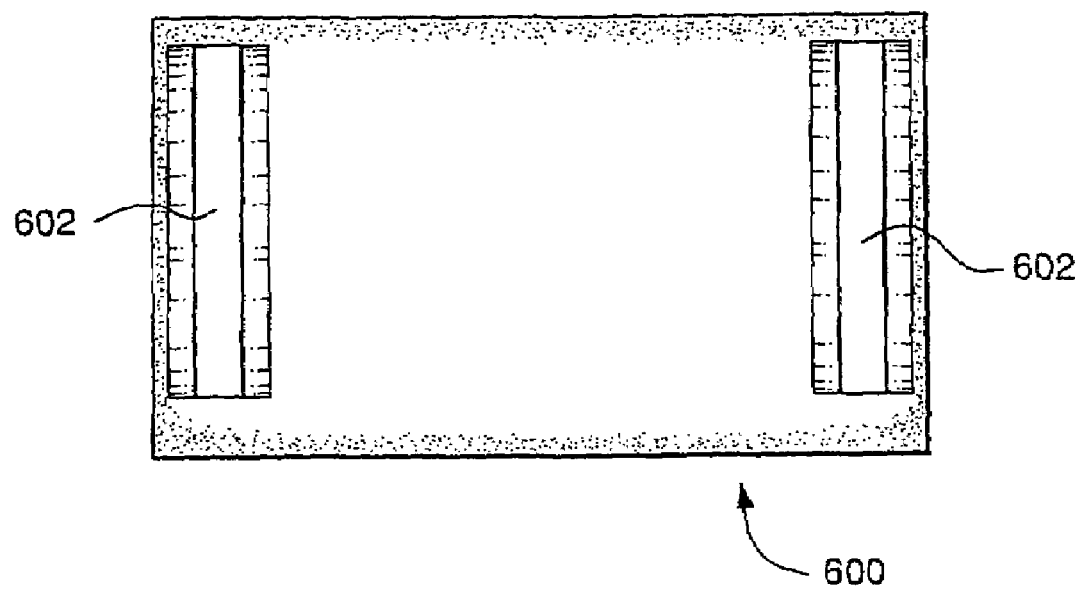
FIG. 15A shows a top view of an exemplary comfort device.
Figure 15B:
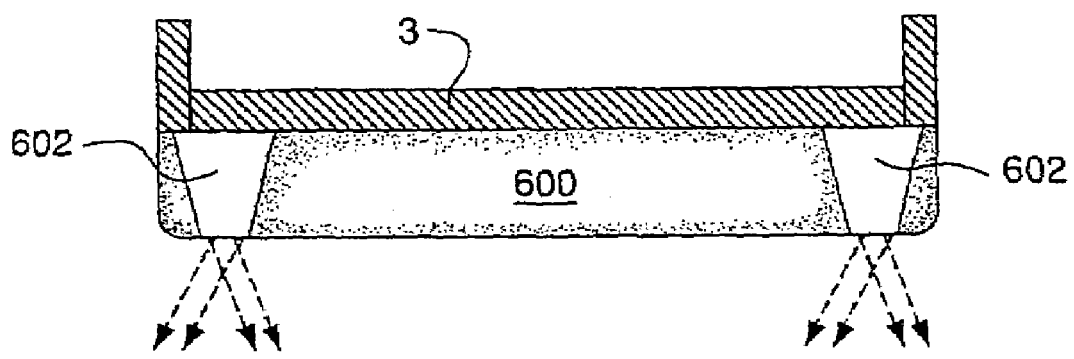
FIG. 15B shows a section view of the exemplary comfort device assembled on a compression paddle.

FIG. 15A shows a top view an exemplary comfort device for a compression paddle. The comfort device 600 of FIG. 15A comprises a compressible material and has at least one opening, 602 that permits visible light to pass through. The compressible material is x-ray transparent. The visible light emanating from the x-ray tube assembly passing through the comfort device facilitates positioning of a breast on the bucky. FIG. 15B shows a section view of the exemplary comfort device 600 having at least one opening 602 through which visible light can be transmitted, assembled on a compression paddle 3.

Figure 16A:
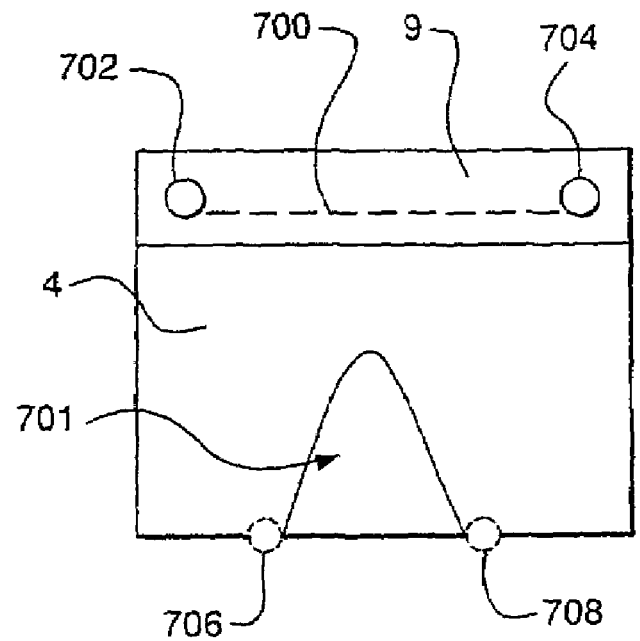
FIGS. 16A and 16B depict a schematic top view of a bucky and a retainer.
Figure 16B:
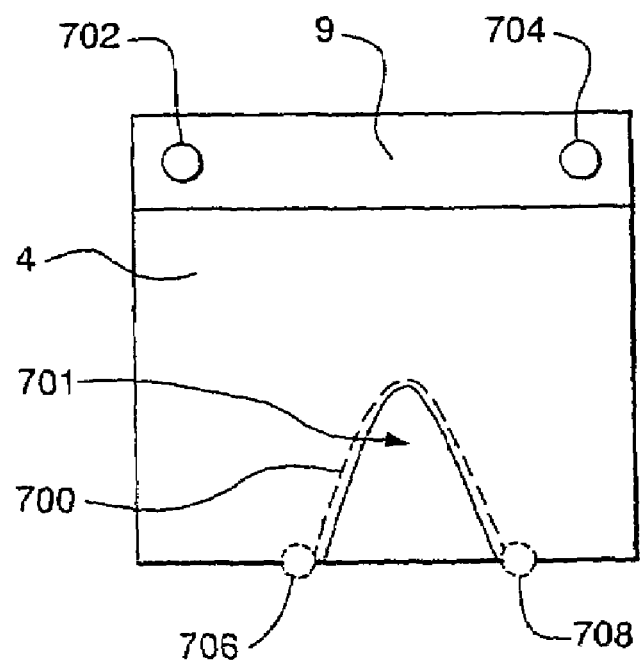

FIG. 16A is a schematic top view of a breast 701 positioned for mammography on a bucky 4 and a retainer 700 whose ends are attached on the bucky in an area 9 that is outside of the imaging area. For use, in one example, the retainer is removed from a first position on the bucky, attached between anchors 702 and 704. It is stretched over the peripheral surface of the breast and anchored in a second position between anchors 706 and 708, that are located along the outer surface of the bucky as shown in FIG. 16B. Used this way, the retainer holds the breast in place on the bucky and less compression force is required, thereby reducing patient discomfort. Generally, the retainer is a strip of stretchable, compressible material. By its stretchable and compressible nature, the retainer can adapt to and hold in place any size and shape breast. The retainer substantially conforms to the surface of the breast where it is placed. The retainer, in use, will therefore, have a concave shape to it as it fits over the peripheral surface of the breast. It is understood that the peripheral surface of the breast includes not only the portion of the breast that is not in contact with the compression paddle and imaging surface upon compression, but also to the extent that the retainer extends beyond such area, adjacent portions of the breast that contact the compression paddle and imaging surface are also included. In practice, it is desirable that the retainer conforms above and below the breast to ensure that diagnostic features in the edges of the breast are captured in the mammogram.

In a preferred embodiment, the retainer is a stretchable strip of x-ray transparent compressible material, suitable for the purpose of preventing the breast from moving during exposure and permitting less compression force to be used. In another preferred embodiment, the retainer is a stretchable strip of x-ray attenuating compressible material. In some examples, the x-ray linear attenuation coefficient of the compressible material approximates that of soft tissue. When this retainer is used in a similar manner as the x-ray transparent retainer, it holds the breast in place on the bucky providing for use of less compression force and reduced patient discomfort. Moreover, the x-ray attenuation property of the retainer functions as an exposure equalizer to reduce the optical density of the peripheral region of the breast on a mammogram.

Reference to anchors means any fastener device suitable for removably or permanently attaching the retainer material to the bucky. In some instances, it may be desirable to affix the retainer to an outer surface of the bucky. The retainer can be positioned over the peripheral surface of the breast before or after compression by the compression paddle. X-ray exposure to obtain a mammogram is made in the usual manner and the retainer is then removed. A first position of the retainer on the bucky provides easy access for the technologist after positioning the breast; alternatively, the retainer can be stored in any area within easy reach of the technologist. The retainer can be for single use or reusable. The retainer may optionally comprise a radiopaque identifier. For example, the retainer may have radiopaque strips along at least one edge to signify that a retainer has been used. It may be advantageous to use a radiopaque anchor to serve a dual purpose of affixing the retainer and conveying information onto the mammogram. The retainer can be used with other types of mammography comfort devices, including but not limited to, compressible pads, disposable covers, and bolsters. The retainer can be used wit any view of the breast, for example, craniocaudal, lateral, and oblique.

Identifiers as discussed in accordance with the present invention can be used along with all types of comfort devices used in conjunction with all types of imaging equipment. Furthermore, comfort devices can be attached to imaging equipment in various ways without impacting the utility of the comfort device comprising an identifier. It is particularly desirable to use identifiers during mammography where comfort devices are used to alert a radiologist or other medical professional that material was in the path of the x-ray beam which may have impacted the image of the breast. It is understood, however, such an indication may be desirable in other imaging disciplines.

While the invention has been described and illustrated with reference to specific embodiments, those skilled in the art will recognize that modifications and variations may be made without departing from the principles of the invention as described herein and set forth in the following claims.

What is claimed:

1. A mammography unit comprising
a mammography unit compression device comprising a paddle, a light transparent panel that is displaced from a compression surface of said paddle by a gap of gas, and a bolster that comprises a compressible material and substantially surrounds the perimeter of said light transparent panel;
an x-ray source, a bucky, a support column to which said bucky is secured and to which said compression device is adjustably attached; wherein said compression device is located between said x-ray source and said bucky.

2. The mammography unit of claim 1 wherein said light transparent panel further comprises a vent.

3. The mammography unit of claim 1 wherein said bolster further comprises a vent.

4. The mammography unit of claim 1 wherein said light transparent panel further comprises a partially radiopaque identifier that comprises indicia which impart information about said light transparent panel onto a mammogram.

5. The mammography unit of claim 1 wherein said light transparent panel further comprises non-radiopaque position markings.

6. The mammography unit of claim 1 wherein said bolster comprises a first compressible material having a first indentation force deflection value and a second compressible material having a second indentation force deflection value that is different from said first indentation force deflection value.

7. A method for reducing patient discomfort during mammography comprising:
securing a light transparent panel over a mammography unit compression paddle with a bolster that comprises a compressible material and substantially surrounds the perimeter of said light transparent panel;
positioning a patient's breast on a bucky; and
administering a mammogram comprising compressing said breast between said compression paddle and said bucky and transmitting x-rays through said breast.

8. The method of claim 7 wherein said light transparent panel comprises a vent and the steps further comprising flowing a gas warmer than room temperature through said vent.

9. A compression paddle for use with a mammography unit, the paddle comprising
a compression surface;
a light transparent panel displaced from the compression surface; and
a bolster comprising a compressible material wherein the compressible material substantially surrounds the perimeter of the light transparent panel;
wherein the bolster orients the panel generally parallel to the compression surface of the paddle; and
wherein said compressible material has a first indentation force deflection value.

10. The paddle of claim 9 wherein the light transparent panel further comprises a vent.

11. The paddle of claim 9 wherein the bolster further comprises a vent.

12. The paddle of claim 9 further comprising a second bolster comprising a second compressible material having a second indentation force deflection value.

13. The paddle of claim 12 wherein when the paddle exerts a compression force to a non-uniform object; and wherein the light transparent panel angulates relative to the compression surface of the paddle.

14. A mammography unit comprising a mammography unit compression device comprising
a paddle comprising a compression surface;
a light transparent panel displaced from the compression surface by a gap of gas;
a bolster comprising a compressible material wherein the compressible material substantially surrounds the perimeter of the light transparent panel;
an x-ray source;
a bucky; and
a support column to which the bucky is secured and to which the compression device is adjustably attached;
wherein the compression device is located between said x-ray source and the bucky.

15. The mammography unit of claim 14 wherein the light transparent panel further comprises a vent.

16. The mammography unit of claim 14 wherein the bolster further comprises a vent.

17. The mammography unit of claim 14 wherein the bolster comprises a first compressible material having a first indentation force deflection value and a second compressible material having a second indentation force deflection value that is different from said first indentation force defection value.

18. A method for reducing patient discomfort during a mammography comprising:
   securing a light transparent panel to a mammography unit comprising a bucky and a compression paddle having a bolster comprising a compressible material and wherein the compressible material substantially surrounds the perimeter of the light transparent panel;
   positioning a patient's breast on a bucky; and
   administering a mammogram comprising compressing the breast between the light transparent panel and the bucky and transmitting x-rays through the breast.

19. The method of claim 18 wherein the light transparent panel comprises a vent.

20. The method of claim 19 further comprising flowing a gas through the vent.

21. The method of claim 20 wherein the gas is warmer than room temperature.

* * * * *